(12) United States Patent
Yang et al.

(10) Patent No.: US 11,698,329 B2
(45) Date of Patent: Jul. 11, 2023

(54) VERTICAL COUNTERFORCE LOADING DEVICE FOR LARGE-TONNAGE SOIL MATERIAL LOAD TEST AND LOADING METHOD THEREOF

(71) Applicant: China Institute of Water Resources and Hydropower Research, Beijing (CN)

(72) Inventors: Zhengquan Yang, Beijing (CN); Qiwang Liu, Beijing (CN); Jianming Zhao, Beijing (CN); Xiaosheng Liu, Beijing (CN); Rongfeng Ma, Beijing (CN); Yusheng Yang, Beijing (CN); Hongjun Li, Beijing (CN); Xiangqian Liang, Beijing (CN); Long Wang, Beijing (CN); Kaibin Zhu, Beijing (CN); Ming Zhai, Beijing (CN); Chaoqun Huang, Beijing (CN); Qing Zhang, Beijing (CN)

(73) Assignee: China Institute of Water Resources and Hydropower Research, Beijing (CN)

( * ) Notice: Subject to any disclaimer, the term of this patent is extended or adjusted under 35 U.S.C. 154(b) by 141 days.

(21) Appl. No.: 17/353,826

(22) Filed: Jun. 22, 2021

(65) Prior Publication Data
US 2022/0011205 A1 Jan. 13, 2022

(30) Foreign Application Priority Data
Jul. 9, 2020 (CN) .......................... 202010657321.4

(51) Int. Cl.
*G01N 3/08* (2006.01)
*G01N 3/02* (2006.01)

(52) U.S. Cl.
CPC ................. *G01N 3/08* (2013.01); *G01N 3/02* (2013.01)

(58) Field of Classification Search
None
See application file for complete search history.

(56) References Cited

U.S. PATENT DOCUMENTS

2004/0118199 A1* 6/2004 Frost ..................... G01S 13/931
73/152.52
2008/0276715 A1* 11/2008 Tombazzi ........... G01M 99/007
73/760

FOREIGN PATENT DOCUMENTS

CN 204116201 * 1/2015
CN 206512764 * 9/2017

* cited by examiner

*Primary Examiner* — David Z Huang
*Assistant Examiner* — Nigel H Plumb
(74) *Attorney, Agent, or Firm* — Bayramoglu Law Offices LLC

(57) ABSTRACT

The vertical counterforce loading device includes a concrete support member, four transfer components, four connection components, a vertical force transmission component and a load test soil layer. The concrete support member is formed by pouring and concreting below the load test soil layer. The four transfer components are divided into two groups to be symmetrically and parallelly anchored in the concrete support member. The vertical force transmission component includes a load plate, a jack, a primary beam and a secondary beam arranged in sequence from bottom to top. The load plate is installed on the load test soil layer. Two secondary beams are connected crosswise to both ends of the primary beam, where end portions of the secondary beams are respectively connected to second ends of the connection (Continued)

components through reinforcement components. The device can improve work efficiency, reduce construction costs and improve safety.

12 Claims, 3 Drawing Sheets

VERTICAL COUNTERFORCE LOADING DEVICE FOR LARGE-TONNAGE SOIL MATERIAL LOAD TEST AND LOADING METHOD THEREOF

CROSS REFERENCE TO THE RELATED APPLICATIONS

This application is based upon and claims priority to Chinese Patent Application No. 202010657321.4, filed on Jul. 9, 2020, the entire contents of which are incorporated herein by reference.

TECHNICAL FIELD

The present invention relates to the technical field of science and engineering application, and in particular to a vertical counterforce loading device for a large-tonnage soil material load test and a loading method thereof.

BACKGROUND

In order to study the bearing capacity and deformation resistance of a natural soil layer and an artificial filling soil layer, and to determine the corresponding characteristic parameters, it is necessary to carry out a load test on a soil layer having a certain thickness. The soil material load test is widely used in civil works, such as civil construction engineering, water conservancy and hydropower engineering, road and railway engineering, port engineering, airport engineering and military facilities engineering. The soil material load test includes the scientific test for studying the corresponding engineering characteristics of soil materials and the engineering test for determining the parameters of the engineering design and construction.

The load test is used in the soil materials filling engineering such as the earth-rock-filled dam. According to the basic principle of the load test, a vertical load is applied to the soil layer through a counterforce mechanism so as to determine respective bearing capacity indexes and compression deformation characteristic indexes of the soil layer. These characteristic indexes are mainly determined based on the load-settlement relation curve (i.e. P-S relation curve) of the measured soil layer, and this relation curve represents the vertical deformation process of a surface load plate of the soil layer under the effect of different vertical loads.

In the modern water conservancy and hydropower projects, because the soil material for the construction of the earth-rock-filled dam has a relatively large particle size, the diameter of the load plate in the soil material load test is typically set to be large to satisfy the proportional relationship between the diameter of the load plate in the load test and a maximum particle size of the soil material according to the test standard. Furthermore, the bearing capacity and the deformation resistance of the macro-aggregated soil material itself are very large. Thus, in the load test of a large-scale load plate of the macro-aggregated soil, in order to obtain the ideal load-settlement relation curve of the load test for the dam materials in engineering practice, a relatively large vertical load needs to be applied in the load test, and this load is provided by a vertical loading mechanism. According to the engineering experience, in order to obtain the ideal P-S relation curve, a circular load plate with a diameter of 1.5 m needs the vertical load of about 1000 tons provided by the test loading mechanism, which belongs to a large or super large test in test scale.

The existing vertical counterforce large-tonnage loading mechanism used in the load test provides the large-tonnage vertical counterforce required by the test through pile-loading and counterforce anchor piling methods.

As for the pile-loading method, it is generally applied to the relatively low vertical loading level, such as the load test within 300 tons. When the load test requires the large-tonnage vertical counterforce, such as the macro-aggregated soil load test for earth-rock-filled dam construction, the scale of the required ballast will be very large. The large-scale pile-loading has the following disadvantages: first, the low work efficiency, because a large number of sandbags or heavy blocks need to be piled up, which takes a long time and requires much labor; second, the potential safety hazard, because the volume of accumulation increases with the increase of tonnage, the accumulation is likely to overturn during the vertical loading test, which brings great hidden danger to the safety of personnel and equipment; third, the high costs of manpower and safeguard measures in the pile-loading test, which causes a significant increase in the total cost of the test.

As for the counterforce anchor piling method, in order to provide a large-tonnage vertical counterforce, the test preparation time will be greatly increased. In the counterforce anchor piling method, a counterforce pile is driven into the test site, and generally there are four piles in one test site, and a friction or anchoring force between the counterforce anchor pile and the soil is used to provide the vertical pulling resistance for a piling body, thereby generating the large-tonnage vertical counterforce required by the test. The construction of counterforce anchor piling needs to go through a series of processes, such as drilling, fabrication and installation of the reinforcement cage, perfusion molding of the piling body and maintenance, which requires high time and economic costs. Moreover, in order to ensure the quality of the test soil layer formed by the soil material, the construction work of the counterforce pile has to start after the test soil layer is formed, and it is inconvenient to regulate the work time. As for the counterforce anchor pile, when a relatively large counterforce is required, an anchoring depth and an end volume increase, or multiple counterforce anchor rods is driven into a smaller range, which results in poor construction operability, and high time and economic costs of the piling body construction.

Therefore, the present invention provides a safe and simple loading device for a large-tonnage vertical counterforce in a soil material load test, which can effectively solve the problems of low work efficiency, high load construction costs and great potential safety hazard existing in the pile-loading method and the counterforce anchor piling method, and it is especially suitable for on-site load tests with relatively poor work conditions.

SUMMARY

A purpose of the present invention is to provide a vertical counterforce loading device for a large-tonnage soil material load test and a loading method thereof. The own weight of a load test object, that is, a tested soil layer, is used to provide the large-tonnage vertical counterforce required by the load test, so as to solve the problem of the force supplying source of the large-tonnage vertical counterforce in the soil material load test.

The purpose of the present invention is realized through the following technical solutions.

A vertical counterforce loading device for a large-tonnage soil material load test includes a concrete support member, four transfer components, four connection components, a vertical force transmission component and a load test soil layer. The concrete support member is formed by pouring and concreting below the load test soil layer. The four transfer components are divided into two groups to be symmetrically and parallelly anchored in the concrete support member. A first end of any one of the connection components is connected to any one of the transfer components, and a second end of any one of the connection components is connected to the vertical force transmission component.

The vertical force transmission component includes a load plate, a jack, a primary beam and a secondary beam that are arranged in sequence from bottom to top. The load plate is installed on the load test soil layer. The number of the secondary beams is two. The two secondary beams are connected crosswise to both ends of the primary beam, and end portions of the two secondary beams are respectively connected to the second ends of the four connection components through reinforcement components.

In the present invention, after the jack in the vertical force transmission component is started, the primary beam and the secondary beam are lifted up. The secondary beam transmits a force to the connection component. The connection component drives the transfer component anchored in the concrete support member to lift the concrete support member up. The weight of the load test soil layer is used to provide a pulling resistance to prevent the concrete support member from moving upwards. When the jack is limited in the lifting process, a vertical pressure is generated on the load plate, and the load plate acts to apply the vertical pressure on the load test soil layer, which realizes the purpose of applying a large-tonnage vertical load to the load test soil layer.

Further, the concrete support member is a member formed by pouring and concreting reinforced concrete, and the connection component is a connecting pole made of solid square steel.

The advantages of the above preferred solution are as follows. The connection component is the connecting pole made of solid square steel, which simplifies and expedites the construction process, and has better safety and lower time and economic costs than the pile-loading method and counterforce anchoring method.

Further, the transfer component includes a first transfer plate and a second transfer plate, the first transfer plate and the second transfer plate cross each other and are welded to constitute a cross transfer plate. Both the first transfer plate and the second transfer plate are made of solid square steel. The first end of the connection component is welded to a center of the cross transfer plate.

The advantages of the above preferred solution as follows. A contact area between the transfer component and the concrete support member can be increased, thereby improving the stability performance.

Further, the reinforcement component includes a ribbed steel plate and a locking fastener. The locking fastener includes a U-shaped steel rod and a nut. The ribbed steel plate is welded to the second end of the connection component, and the ribbed steel plate is provided with a through hole fitting with the U-shaped steel rod. The U-shaped steel rod passes through an end portion of the secondary beam. The through hole fits with the nut to realize the fixed connection between the connection component and the secondary beam.

The advantages of the above preferred solution are as follows. The reinforcement component can realize the fixed connection between the second end of the connection component and the end portion of the secondary beam, so that the concrete support member and the vertical force transmission component are connected to constitute the main part of the device for a soil material load test.

Further, a gasket is disposed between the nut and the ribbed steel plate.

The advantages of the above preferred solution are as follows. In the present invention, the gasket can protect the ribbed steel plate from the damage caused by the nut and the U-shaped steel rod in a loading process. When the secondary beam is lifted up, the contact area between the nut and the ribbed steel plate can be increased, so that the nut and the ribbed steel plate are connected together tightly, and the loading performance is more stable.

Further, a filling soil layer is disposed on a periphery of the concrete support member.

The advantages of the above preferred solution are as follows. The filling soil layer is configured to strengthen the stability of the concrete support member.

A vertical counterforce loading method for a large-tonnage soil material load test by using the loading device includes the following steps:

S1. Installing the transfer component and the connection component: on a planned test site, before compacting the load test soil layer, putting four transfer components in place below the load test soil layer, and then welding and connecting the first end of the connection component to the center of the transfer component.

S2. Pouring and concreting the concrete support member below the load test soil layer.

S3. Laying the filling soil layer: filling the soil at the site around the concrete support member and compacting the soil to form the filling soil layer.

S4. Constructing the load test soil layer according to the requirements of test procedures.

S5. Arranging and constructing the vertical force transmission component: installing the load plate, the jack, the primary beam and the secondary beam on the load test soil layer in sequence, and fixedly connecting the secondary beam to the second end of the connection component through the reinforcement component.

S6. Performing the load test: starting the jack, lifting the primary beam and the secondary beam up, transmitting a force to the connection component by the secondary beam, driving the transfer component anchored in the concrete support member by the connection component to lift the concrete support member up, providing a pulling resistance to prevent the concrete support member from moving upwards under the effect of a weight of the load test soil layer, when the jack is limited in the lifting process, generating vertical pressure on the load plate, and enabling the load plate to apply the vertical pressure on the load test soil layer.

Advantages of the present invention are as follows:

1) In the vertical counterforce loading device for the large-tonnage soil material load test of the present invention, the concrete support member thereof is formed by pouring and concreting below the load test soil layer to support the test soil layer. The transfer component is anchored in the concrete support member. The transfer component is connected to the vertical force transmission component through the connection component. The transfer component is divided into two symmetrical and parallel groups. After the jack in the vertical force transmission component is started, the primary beam and the secondary beam are lifted up. The secondary beam transmits a force to the connection component, such that the connection component drives the transfer component anchored in the concrete support member to lift the concrete support member up. The weight of the load test soil layer is used to provide a pulling resistance to prevent the concrete support member from moving upwards. When the jack is limited in the lifting process, a vertical pressure will be generated on the load plate, and the load plate acts to apply the vertical pressure on the load test soil layer, thereby realizing the purpose of applying a large-tonnage vertical load to the load test soil layer.

2) According to the test method of the present invention, the construction time of the concrete support member and the connection component is about 15 days. After offering a measure of protection, the construction of the load test soil layer can be started. Besides, the concrete is being maintained during this period of time, such that the maintenance of the concrete support member and the construction of the test soil layer can be performed at the same time, which can greatly shorten the total test cycle. The test procedure and time arrangement of the present invention are flexible, and there is no overturning phenomenon caused by the accumulation of heavy objects in the test process, so as to greatly improve the test efficiency while ensuring safety.

Figure 1:
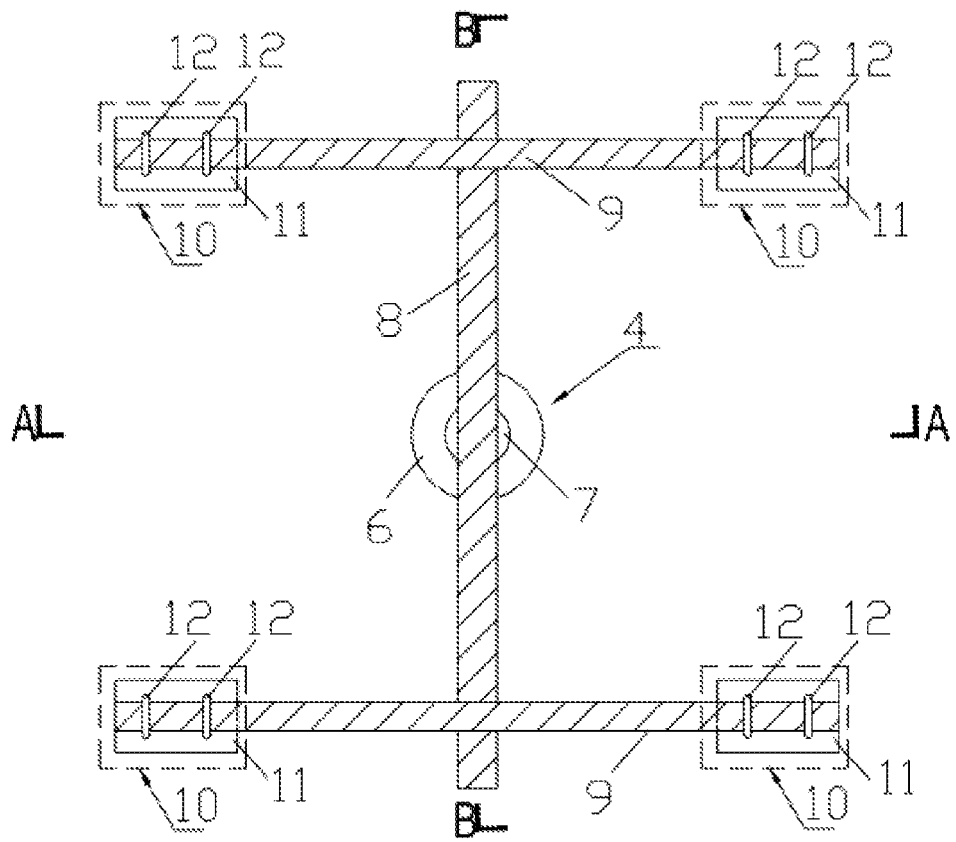
FIG. 1 is a top view of an overall structure of the present invention.

In the drawings, 1—concrete support member, 2—transfer component, 201—first transfer plate, 202—second transfer plate, 3—connection component, 4—vertical force transmission component, 5—load test soil layer, 6—load plate, 7—jack, 8—primary beam, 9—secondary beam, 10—reinforcement component, 11—ribbed steel plate, 12—locking fastener, 13—U-shaped steel rod, 14—nut, 15—through hole, 16—gasket, and 17—filling soil layer.

DETAILED DESCRIPTION OF EMBODIMENTS

The technical solutions of the present invention will be clearly and completely described below in conjunction with embodiments, and obviously, the described embodiments are only a part of embodiments of the present invention, rather than all embodiments. Based on the embodiments of the present invention, all the other embodiments obtained by those skilled in the art on the premise that no creative effort is exerted, belong to scopes protected by the present invention.

Embodiment 1

Referring to FIGS. 1-5, the present invention provides a technical solution.

Figure 2:
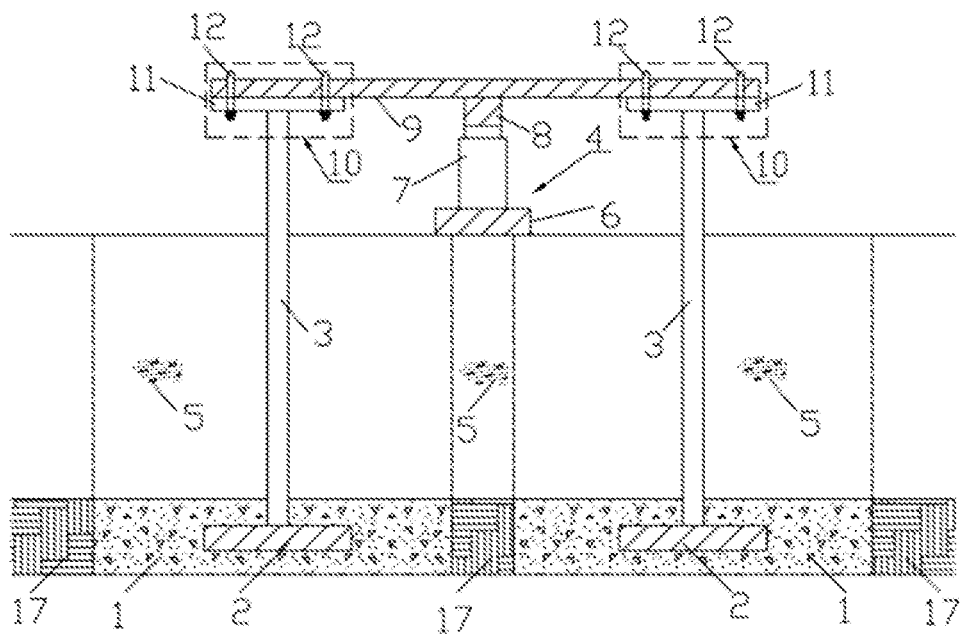
FIG. 2 is a sectional view taken from the line A-A in FIG. 1 of the present invention.
Figure 3:
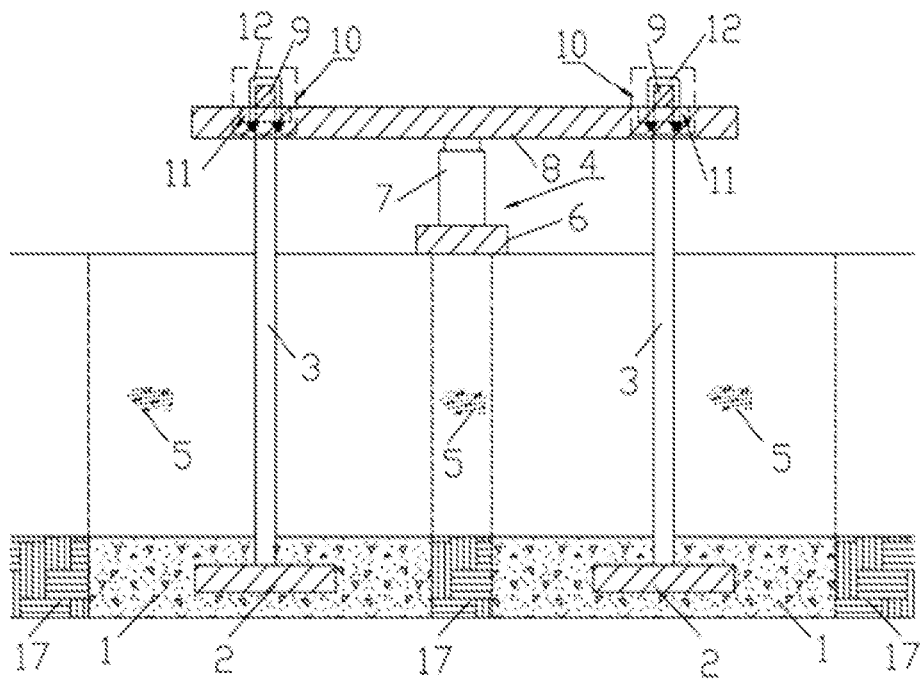
FIG. 3 is a sectional view taken from the line B-B in FIG. 1 of the present invention.

According to FIGS. 1-3, a vertical counterforce loading device for a large-tonnage soil material load test includes the concrete support member 1, four transfer components 2, four connection components 3, the vertical force transmission component 4 and the load test soil layer 5. The concrete support member 1 is formed by pouring and concreting below the load test soil layer 5. The four transfer components 2 are divided into two groups to be symmetrically and parallelly anchored in the concrete support member 1. The first end of any one of the connection components 3 is connected to any one of the transfer components 2, and the second end of any one of the connection components 3 is connected to the vertical force transmission component 4.

The vertical force transmission component 4 includes the load plate 6, the jack 7, the primary beam 8 and the secondary beam 9 that are arranged in sequence from bottom to top. The load plate 6 is installed on the load test soil layer 5. The number of the secondary beams 9 is two. The two secondary beams 9 are connected crosswise to both ends of the primary beam 8. The end portions of the two secondary beams 9 are respectively connected to the second ends of the four connection components 3 through reinforcement components 10.

In the vertical counterforce loading device for the large-tonnage soil material load test of the present invention, the concrete support member 1 thereof is formed by pouring and concreting below the load test soil layer 5 to support the test soil layer. The transfer component 2 is anchored in the concrete support member 1. The transfer component 2 is connected to the vertical force transmission component 4 through the connection component 3. The transfer component 2 is divided into two symmetrical and parallel groups. After the jack 7 in the vertical force transmission component 4 is started, the primary beam 8 and the secondary beam 9 are lifted up. The secondary beam 9 transmits a force to the connection component 3, and then the connection component 3 drives the transfer component 2 anchored in the concrete support member 1 to lift the concrete support member 1 up. The weight of the load test soil layer 5 is used to provide a pulling resistance to prevent the concrete support member 1 from moving upwards. When the jack 7 is limited in the lifting process, a vertical pressure will be generated on the load plate 6, and the load plate 6 acts to apply the vertical pressure on the load test soil layer 5, that is, the purpose of applying a large-tonnage vertical load to the load test soil layer 5 is realized.

In order to provide the large-tonnage vertical loading force to the load plate, the present invention still employs the jack 7, the primary beam 8 and the secondary beam 9 to transmit the load provided that four mechanisms capable of bearing 1000 tons of vertical counterforce are connected at end portions of two secondary beams 9, that is to say, the vertical force transmission component 4 of the present invention needs to bear 1000 tons of vertical force.

According to FIGS. 1-3, the concrete support member 1 is a member formed by pouring reinforced concrete, and the connection component 3 is a connecting pole made of solid square steel.

In the present invention, the concrete support member 1 is a member formed by pouring reinforced concrete, and the connection component 3 is the connecting pole made of solid square steel, which simplifies and expedites the construction process, and has characteristics of high safety, low time and economic costs compared with the pile-loading method and counterforce anchoring method. The present invention is especially suitable for on-site load tests and direct shear tests under relatively poor work conditions.

Figure 4:
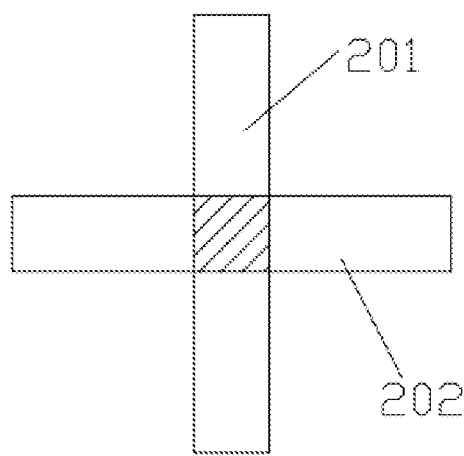
FIG. 4 is a structural schematic diagram of a transfer component of the present invention.

According to FIG. 4, the transfer component 2 includes the first transfer plate 201 and the second transfer plate 202. The first transfer plate 201 and the second transfer plate 202 cross each other and are welded to constitute a cross transfer plate. Both the first transfer plate 201 and the second transfer plate 202 are made of solid square steel, and the first end of the connection component 3 is welded to a center of the cross transfer plate.

The transfer component 2 of the present invention is a cross transfer plate formed by crossing and welding the first transfer plate 201 and the second transfer plate 202, which can increase the contact area between the transfer component 2 and the concrete support member 1, and improve the stability performance.

Figure 5:
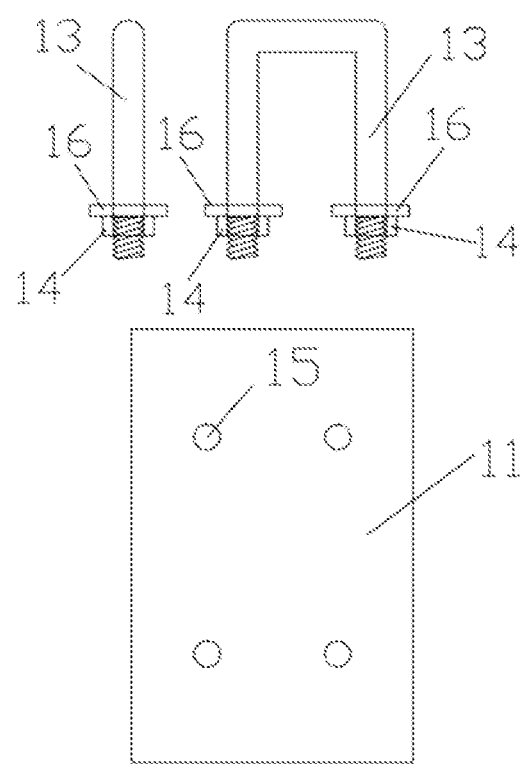
FIG. 5 is a structural schematic diagram of a reinforcement component of the present invention.

According to FIG. 5, the reinforcement component 10 includes the ribbed steel plate 11 and the locking fastener 12. The locking fastener 12 includes the U-shaped steel rod 13 and the nut 14. The ribbed steel plate 11 is welded to the second end of the connection component 3. The ribbed steel plate 11 is provided with the through hole 15 fitting with the U-shaped steel rod 13. The U-shaped steel rod 13 passes through an end portion of the secondary beam 9. The through hole 15 fits with the nut 14 to realize the fixed connection between the connection component 3 and the secondary beam 9.

In the present invention, the second end of the connection component 3 is fixedly connected to the end portion of the secondary beam 9 by the reinforcement component 10, so that the concrete support member 1 and the vertical force transmission component 4 are connected to constitute the main part of the device for a soil material load test.

According to FIG. 5, the gasket 16 is disposed between the nut 14 and the ribbed steel plate 11.

In the present invention, the gasket 16 can protect the ribbed steel plate 11 from the damage caused by the nut 14 and U-shaped steel rod 13 in a loading process. When the secondary beam is lifted up, the contact area between the nut 14 and the ribbed steel plate 11 increases, so that the nut 14 and the ribbed steel plate 11 are connected together tightly, and the loading performance is more stable.

According to FIGS. 2-3, the filling soil layer 17 is disposed on a periphery of the concrete support member 1.

The laying of the filling soil layer 17 of the present invention can strengthen the stability of the concrete support member 1.

A vertical counterforce loading method for a large-tonnage soil material load test by using the loading device includes the following steps.

S1. Installing the transfer component 2 and the connection component 3: on the planned test site, before compacting the load test soil layer 5, the four transfer components 2 are put in place below the load test soil layer 5, and then the first end of the connection component 3 is welded and connected to the center of the transfer component 2.

Particularly, the connection component 3 is made of solid square steel. The size and length of the cross section of the connection component 3 are determined according to a vertical pull-up force and the height of the load test mechanism. The connection component 3 and the transfer component 2 are anchored and connected by means of welding.

S2. Pouring and concreting the concrete support member 1 below the load test soil layer 5.

The concrete support member 1, the transfer component 2 and the connection component 3 should be constructed according to a design structure and size, and the size thereof is determined according to the maximum vertical loading force required by the load test and in conjunction with a plane size of the load test soil layer 5 and a thickness of the test soil layer. According to the engineering construction standard, there are specific requirements on how to determine the size, which will not be repeated herein. The following requirements should be satisfied: a geometric shape of the concrete support member 1 on the plane view should be conducive to the construction and satisfy the test requirement, an area of the concrete support member 1 on the plane view needs to ensure that the total weight of the overlying soil on the concrete support member 1 is greater than a pulling force of a single pile, that is, the single connection component 3, and the safety margin satisfying the test requirement is reserved; a thickness of the concrete support member 1 should satisfy the test requirement for deformation; the connection between the transfer component 2 and the concrete support member 1 need to ensure that the connection component 3 is not pulled out from the concrete support member 1 under the pull-up effect of a maximum pull-up force.

Particularly, after the transfer component 2 is put in place and welded with the connection component 3, the concrete pouring construction of the concrete support member 1 should be performed. The concrete support member 1 below the load test soil layer 5 is formed by pouring and concreting according to the design structure and size. The concrete support member 1 is used to support the upper soil body thereon. The bottom end of the connection component 3 is anchored inside the concrete support member 1 through the transfer component 2.

S3. Laying the filling soil layer 17: the soil is filled and compacted at the site around the concrete support member 1 to form the filling soil layer 17.

The crest elevation of the filling soil layer 17 should be flush with a surface of the concrete support member 1, and the compaction and flatness requirements of the filling soil layer 17 need to satisfy the relevant requirement of the load test.

S4. Constructing the load test soil layer 5 according to the requirements of test procedures.

Particularly, the filling size and compaction standard of the test soil layer are determined according to the relevant specification standard of the load test, and the collision between the construction machinery and the connection component 3 should be avoided in the construction process.

S5. Arranging and constructing the vertical force transmission component 4: the load plate 6, the jack 7, the primary beam 8 and the secondary beam 9 are installed on the load test soil layer 5 in sequence, and the secondary beam 9 is fixedly connected to the second end of the connection component 3 through the reinforcement component 10.

Particularly, after the construction of the load test soil layer 5 is finished according to the requirement, the load plate 6, the jack 7, the primary beam 8 and the secondary beam 9 are installed in sequence at the position of the test point. The ribbed steel plate 11 is first welded at the top end of the connection component 3, wherein the top of the ribbed steel plate 11 is ensured to be flush with a top of the primary beam 8. Then, the ribbed steel plate 11 is welded to the second end of the connection component 3. Two U-shaped steel rods 13 are installed across the secondary beam 9 and pass through the through hole 15 on the ribbed steel plate 11. The U-shaped steel rods 13 are fixed on the ribbed steel plate 11 by using the nuts 14 and the gaskets 16, so as to realize a firm connection between the end portion of the secondary beam 9 and the second end of the connection component 3.

The size of the cross section of the U-shaped steel rod 13 and the sizes of the thread and the matching nut 14 are determined according to the pulling resistance of the single pile of the force transmission mechanism.

S6. Performing the load test: the jack 7 is started to lift the primary beam 8 and the secondary beam 9 up, the secondary beam 9 transmits a force to the connection component 3, such that the connection component 3 drives the transfer component 2 anchored in the concrete support member 1 to lift the concrete support member 1 up. The pulling resistance to prevent the concrete support member 1 from moving upwards is provided by the weight of the load test soil layer 5. When the jack 7 is limited in the lifting process, a vertical pressure will be generated on the load plate 6, and then the load plate 6 acts to apply the vertical pressure on the load test soil layer 5, thereby realizing the purpose of applying a large-tonnage vertical load to the load test soil layer 5.

Soil Material Load Test

An artificial compacted soil layer with a thickness of 5 m and a size of 12×16 m is selected as the test site. The requirement for the maximum vertical load is 1000 tons. The comparison data obtained by comparing the present invention with the traditional pile-loading method and the counterforce anchor loading method is as follows.

Time cost: it takes about one month to pack, transport and install sand bags by the pile-loading method, but the load test soil layer 5 must be completed before the construction of a pile-loading mechanism. Similar to the pile-loading method, the construction of the counterforce anchor piling method must be started after the load test soil layer 5 is completed. The total time of construction and concrete curing is about 3 months.

However, in the present invention, the construction time of the concrete support member 1, the transfer component 2 and the connection component 3 is about 15 days, the construction of the load test soil layer 5 can be started as long as a little protection is provided. Also, the maintenance of the concrete can be performed during this period of time, such that the maintenance of the concrete support member 1 and the construction of the test soil layer can be performed at the same time, which can greatly shorten the total test cycle.

Economic cost: the total cost of manpower together with the loading platform of the pile-loading method is about 300,000 RMB; the cost of a single pile of the counterforce piling method is about 200,000 RMB, and the total cost of four piles in one test is about 800,000 RMB.

However, in the present invention, the total cost of a set of the concrete support member 1, the transfer component 2 and the connection component 3 of the present invention is about 70,000 to 80,000 RMB, and the total cost is about 300,000 RMB, which is roughly equivalent to the pile-loading method.

Safety: the safety of the large-tonnage pile-loading method is relatively poor, there are potential safety hazards in the construction of the pile-loading body and the test process, and thus, the large-tonnage pile-loading method is rarely used in actual projects. However, the loading method of the present invention uses the own weight of the test soil layer to provide a counterforce source so the loading method of the present invention is surely safe in the process of both the construction and the test of the loading mechanism.

Based on the above comprehensive considerations of time cost, economic benefit, work safety and the like, the pile-loading method is equivalent to the method of the present invention in the economic cost, but the pile-loading method has a great potential safety hazard, and the test procedure and time arrangement of the pile-loading method are not flexible. The counterforce piling method of the present invention is safe, but both the time cost and the economic cost of the test are relatively high, and the procedure arrangement of the test is not flexible.

In summary, the vertical counterforce loading device for the large-tonnage soil material load test of the present invention and the loading method thereof are superior to the traditional mechanisms and loading method in regard to improving the work efficiency and safety, and reducing the test work time and economic costs. The present invention is especially suitable for large-scale projects and relatively poor comprehensive working conditions in the field. Moreover, the present invention has the characteristics of high safety, low time cost, and flexible test procedures and time arrangements.

The present invention provides a vertical load loading mechanism and a large-tonnage vertical load source for the on-site large-scale load test and the direct shear test for artificial filling engineering soil materials. The present invention uses the own weight of the load test soil layer 5 to provide the large-tonnage vertical counterforce required by the load test, it is only necessary to construct the support member and a connecting mechanism for transmitting the counterforce at the bottom of the test soil layer in advance, and the construction is simple and fast.

The above are only the preferred embodiments of the present invention. It should be understood that the present invention is not limited to the way disclosed herein, and the preferred embodiments should not be regarded as the exclusion of other embodiments. The preferred embodiments can be applied to other various combinations, modifications and environments, and can be modified through the above teachings or technology or knowledge in related fields within the concept scope described herein. However, these modifications and changes made by those skilled in the art do not depart from the spirit and scope of the present invention, and should fall within the scope of the claims of the present invention.

What is claimed is:

1. A vertical counterforce loading device for a large-tonnage soil material load test, comprising a concrete support member, four transfer components, four connection components, a vertical force transmission component and a load test soil layer, wherein
    the concrete support member is formed by pouring and concreting below the load test soil layer;
    the four transfer components are divided into two groups to be symmetrically and parallelly anchored in the concrete support member;
    a first end of a given connection component of the four connection components is connected to a given transfer component of the four transfer components, and a second end of the given connection component of the four connection components is connected to the vertical force transmission component; and
    the vertical force transmission component comprises a load plate, a jack, a primary beam and two secondary beams arranged in sequence such that the load plate is at a bottom of the sequence, the jack is above the load plate, the primary beam is above the jack and the two secondary beams are above the primary beam and are at a top of the sequence, wherein the load plate is installed on the load test soil layer, the two secondary beams are connected crosswise to both ends of the primary beam, and end portions of the two secondary beams are respectively connected to second ends of respective two connection components of the four connection components through reinforcement components.

2. The vertical counterforce loading device of claim 1, wherein the concrete support member is a member made of reinforced concrete, and the given connection component is a connecting pole made of solid square steel.

3. The vertical counterforce loading device of claim 2, wherein a filling soil layer is disposed on a periphery of the concrete support member.

4. The vertical counterforce loading device of claim 1, wherein the given transfer component comprises a first transfer plate and a second transfer plate,
the first transfer plate and the second transfer plate cross each other and are welded to constitute a cross transfer plate,
the first transfer plate and the second transfer plate are made of solid square steel, and
the first end of the given connection component is welded to a center of the cross transfer plate.

5. The vertical counterforce loading device of claim 1, wherein a given reinforcement component of the reinforcement components comprises a ribbed steel plate and a locking fastener,
the locking fastener comprises a U-shaped steel rod and a nut,
the ribbed steel plate is welded to the second end of the given connection component,
the ribbed steel plate is provided with a through hole fitting with the U-shaped steel rod,
the U-shaped steel rod passes through an end portion of a given secondary beam of the two secondary beams, and
the through hole fits with the nut to realize a fixed connection between the given connection component and the given secondary beam.

6. The vertical counterforce loading device of claim 5, wherein a gasket is disposed between the nut and the ribbed steel plate.

7. A vertical counterforce loading method for a large-tonnage soil material load test by using the loading device of claim 1, comprising the following steps:
S1: installing the given transfer component and the given connection component: on a planned test site, before compacting the load test soil layer, putting the four transfer components in place below the load test soil layer, and then welding and connecting the first end of the given connection component to a center of the given transfer component;
S2: pouring and concreting the concrete support member below the load test soil layer;
S3: laying a filling soil layer: filling soil at a site around the concrete support member, and compacting the soil to form the filling soil layer;
S4: constructing the load test soil layer according to requirements of test procedures;
S5: arranging and constructing the vertical force transmission component: installing the load plate, the jack, the primary beam and the two secondary beams on the load test soil layer in the sequence, and fixedly connecting a given secondary beam of the two secondary beams to the second end of the given connection component through a given reinforcement component of the reinforcement components;
S6: performing the load test: starting the jack, lifting the primary beam and the two secondary beam up, transmitting a force to the given connection component by the given secondary beam of the two secondary beams, driving the given transfer component anchored in the concrete support member by the given connection component to lift the concrete support member up, providing a pulling resistance to prevent the concrete support member from moving upwards under an effect of a weight of the load test soil layer, when the jack is limited in a lifting process, generating vertical pressure on the load plate, and enabling the load plate to apply the vertical pressure on the load test soil layer.

8. The vertical counterforce loading method of claim 7, wherein the concrete support member concreted at the step S2 is a member made of reinforced concrete, and the given connection component installed at the step S1 is a connecting pole made of solid square steel.

9. The vertical counterforce loading method of claim 8, wherein the filling soil layer laid at the step S3 is disposed on a periphery of the concrete support member.

10. The vertical counterforce loading method of claim 7, wherein the given transfer component installed at the step S1 comprises a first transfer plate and a second transfer plate,
the first transfer plate and the second transfer plate cross each other and are welded to constitute a cross transfer plate,
the first transfer plate and the second transfer plate are made of solid square steel, and
the first end of the given connection component is welded to a center of the cross transfer plate.

11. The vertical counterforce loading method of claim 7, wherein the given reinforcement component, through which the given secondary beam is fixedly connected to the second end of the given connection component at the step S5, comprises a ribbed steel plate and a locking fastener,
the locking fastener comprises a U-shaped steel rod and a nut,
the ribbed steel plate is welded to the second end of the given connection component,
the ribbed steel plate is provided with a through hole fitting with the U-shaped steel rod,
the U-shaped steel rod passes through an end portion of the given secondary beam of the two secondary beams, and
the through hole fits with the nut to realize a fixed connection between the given connection component and the given secondary beam.

12. The vertical counterforce loading method of claim 11, wherein a gasket is disposed between the nut and the ribbed steel plate of the given reinforcement component, through which the given secondary beam is fixedly connected to the second end of the given connection component at the step S5.

* * * * *